US00PP27042P3

(12) United States Plant Patent
Jacobs

(10) Patent No.: US PP27,042 P3
(45) Date of Patent: Aug. 9, 2016

(54) ***CHRYSANTHEMUM* PLANT NAMED 'ZANMUCUP'**

(50) Latin Name: ***Chrysanthemum×morifolium* Ramat.**
Varietal Denomination: Zanmucup

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Breeders B.V., Valkenburg (NL)

( * ) Notice: Subject to any disclaimer, the term of this patent is extended or adjusted under 35 U.S.C. 154(b) by 3 days.

(21) Appl. No.: 14/544,362

(22) Filed: Dec. 30, 2014

(65) Prior Publication Data
US 2016/0192565 P1 Jun. 30, 2016

(51) Int. Cl.
*A01H 5/02* (2006.01)

(52) U.S. Cl.
USPC ..... Plt./289

(58) Field of Classification Search
USPC ..... Plt./289
CPC ..... A01H 5/0255; A01H 5/025
See application file for complete search history.

*Primary Examiner* — Kent L Bell
(74) *Attorney, Agent, or Firm* — Steptoe & Johnson LLP

(57) ABSTRACT

A *chrysanthemum* plant named 'Zanmucup' characterized by its medium sized blooms with intense yellow ray florets and prolific branching; natural season flowering date September 22; blooming for a period of 4 weeks.

3 Drawing Sheets

Botanical designation: *Chrysanthemum×morifolium* Ramat.

Cultivar denomination: 'Zanmucup'.

RELATED CULTIVARS

This new plant cultivar 'Zanmucup' is of the botanical classification *Chrysanthemum×morifolium* Ramat.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmucup'. 'Zanmucup' is a product of a breeding and selection program for outdoor pot mums (garden mums) which had the objective of creating new cultivars with a double type inflorescence, a natural season flowering date around September 22, blooming for a period of 5 weeks. 'Zanmucup' is a seedling resulting from a cross of the female parent 21570 with the male parent 24605. Plants of the new cultivar 'Zanmucup' differ from plants of the female parent in the natural season flowering date; plants of the seedling flower one week earlier than those of the female parent. Plants of the seedling differ from plants of the male parent in inflorescence type; inflorescences of the seedling are double, while those of the male parent are semi-double.

The new and distinct cultivar was discovered and selected as a flowering plant by Henricus Cornelius Maria Jacobs on a cultivated field in Rijsenhout, The Netherlands in 2010. The first act of asexual production of 'Zanmucup' was accomplished when vegetative cuttings from the initial selection in 2010 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
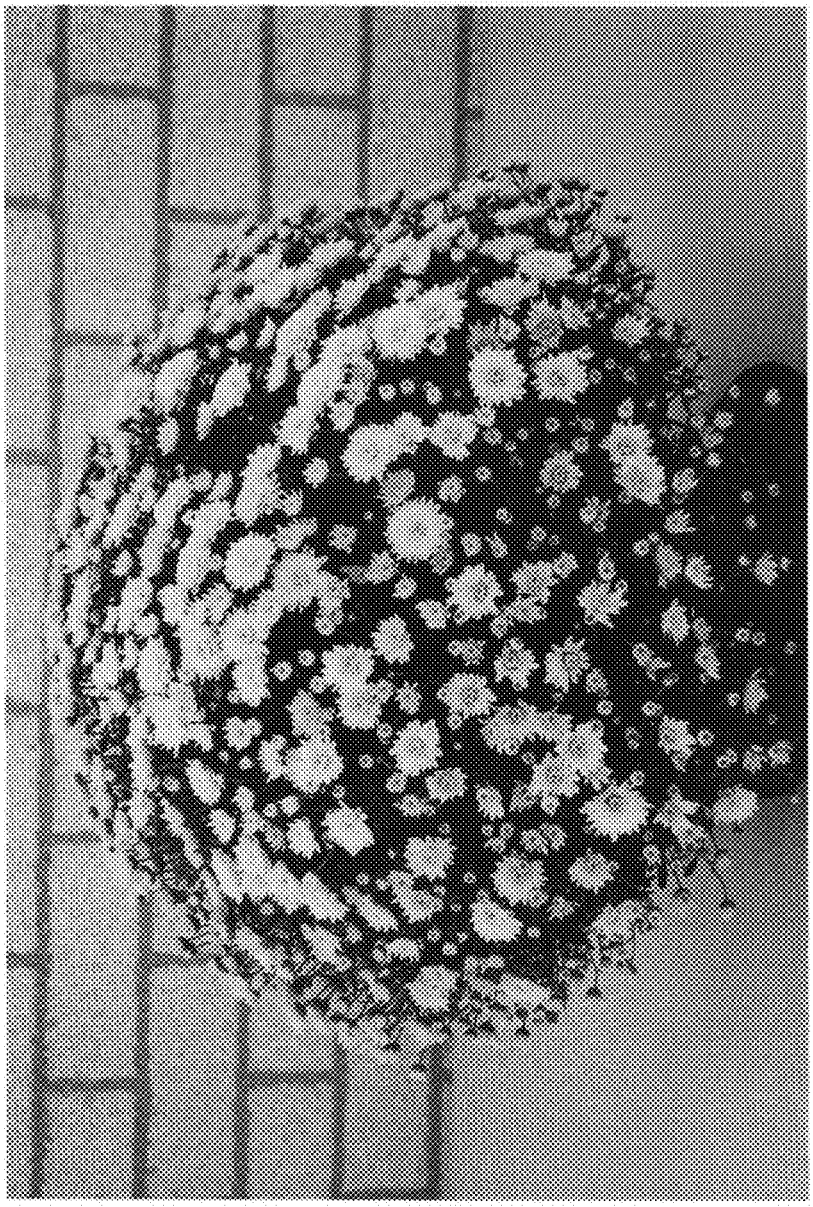
FIG. 1 shows a plant of the cultivar in full bloom.
Figure 2:
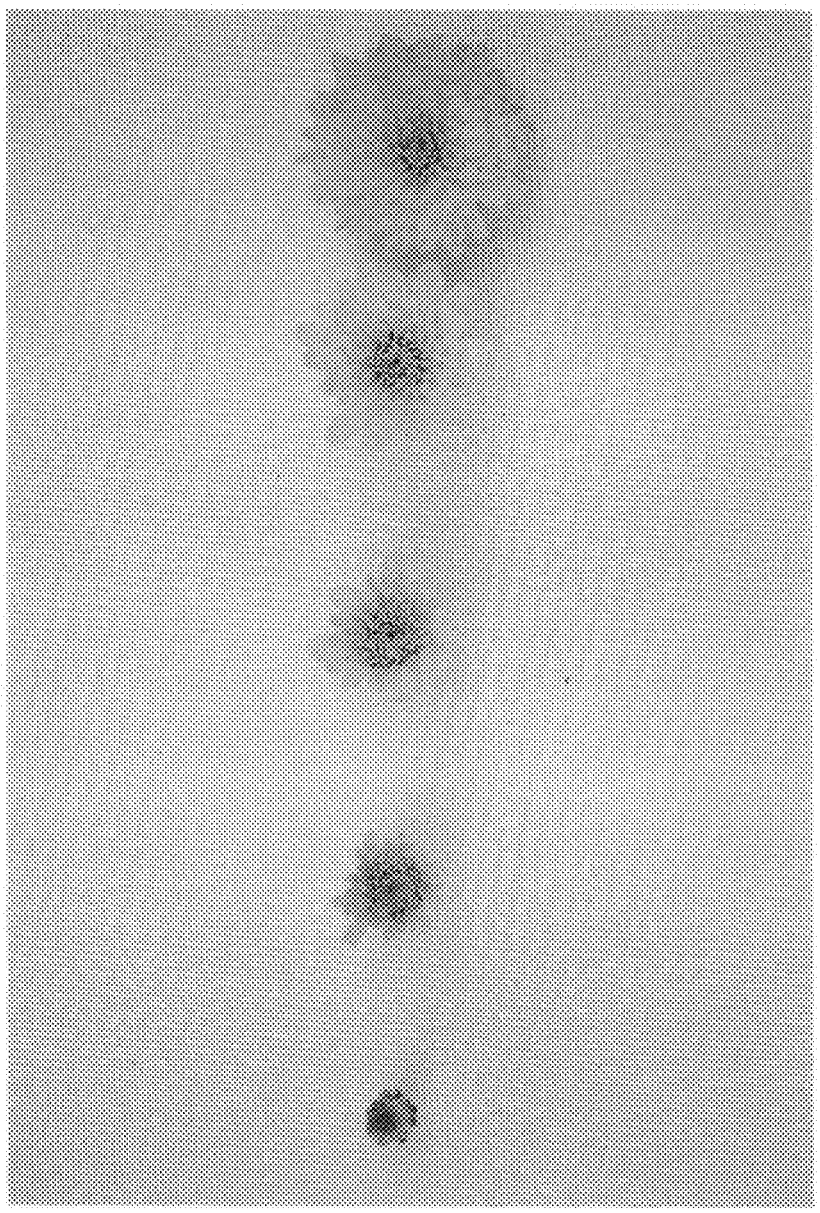
FIG. 2 shows the various stages of bloom of the new cultivar.
Figure 3:
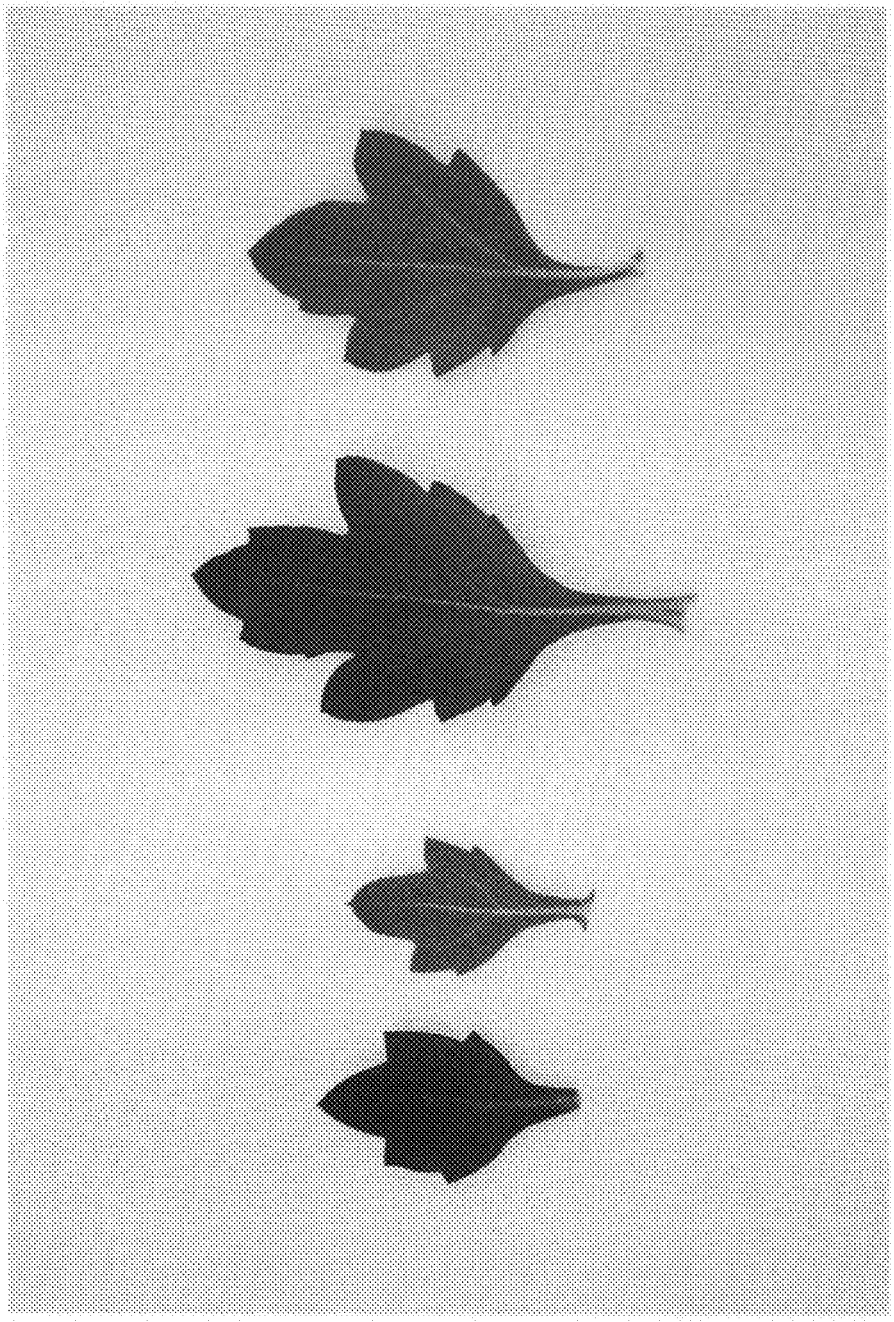
FIG. 3 shows the various stages of foliage of the new cultivar.

The observations and measurements were gathered from plants grown out door in Rijsenhout, The Netherlands, under natural day length and temperature and planted in week 25 in 2014, receiving drip irrigation. The natural blooming date of this crop was September 22. The average height of the plants was 30 cm. No growth retardants were used. No tests were done on disease or insect resistance or susceptibility. No tests were done on cold or drought tolerance. This new variety produces medium sized blooms with intense yellow ray florets blooming for a period of 4 weeks.

From the cultivars known to inventor the most similar existing cultivar in comparison to 'Zanmucup' is 'Zanmustone' (U.S. Plant Pat. No. 22,619). When 'Zanmustone' and 'Zanmucup' are being compared the following difference is noticed: The differences of 'Zanmustone' and 'Zanmucup' are (1) Color ray florets. And (2) Leaf color. (1) Ray-florets of 'Zanmucup' are more deep yellow than those of 'Zanmustone'. (2) Leaves of 'Zanmustone' are more greyish green than those of 'Zanmumcup'.

The following is a description of the plant and characteristics that distinguish 'Zanmucup' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmucup'

| | |
|---|---|
| **Bud** | |
| Size: | Small; cross-section 4 mm, height 3 mm |
| Shape: | Round |
| Texture: | Pubescent |
| Outside color: | Greyed-green 191A |
| **Phyllaries** | |
| Number: | 24, arranged in 3 rows |
| Shape: | Elliptic |
| Apex: | Acute |
| Base: | Truncate |
| Margin: | Entire |
| Color: | Upper side: Greyed-green 189A<br>Lower side: Green 136A |
| Length and width: | 4 mm; 3 mm |
| Texture: | Pubescent |
| **Inflorescences** | |
| Type: | Double |
| Height: | 2 cm |
| Diameter: | 4 cm |
| Peduncle length: | 4-6.5 cm |
| Peduncle color: | Green 136C |
| Peduncle diameter: | 2 mm |
| Peduncle texture: | Pubescent |
| Number per branch: | About 5-6 .inflorescences |
| Duration of flowering: | 4 weeks |
| Seeds: | Produced in small quantities, ovate, Greyed-brown 199A, length 1.5 mm, diameter 0.5 mm |
| Fragrance: | Faint chrysanthemum odor |
| **Color inflorescences** | |
| Center of inflorescence: | Immature stage: Yellow-orange 17A.;<br>Mature stage: Yellow-orange 17A |
| Color of upper side of ray florets: | Yellow 12a |
| Color of lower side of ray florets: | Yellow 8A |
| Tonality from distance: | A garden mum with yellow blooms and a dark yellow center |
| Color of ray florets after aging of the plant: | Yellow-orange 15A |
| **Ray florets** | |
| Texture: | Upper and lower side smooth |
| Number: | 160 |
| Shape: | elliptic |
| Apex: | dentate |
| Base: | acute |
| Cross-section: | flat |
| Longitudinal axis: | straight |
| Length of corolla tube: | 3-4. mm |
| Ray floret margin: | Entire |
| Ray floret length: | 1-2 cm |
| Ray floret width: | 2-5 mm |
| Ratio length/width: | medium |
| Disc florets | absent |
| **Receptacle** | |
| Color: | Yellow-green 145D |
| Shape: | Domed raised |

TABLE 1-continued

Botanical Description of *Chrysanthemum* × *morifolium* Ramat. 'Zanmucup'

| | |
|---|---|
| Height: | 3 mm |
| Diameter: | 3 mm |
| **Reproductive Organs** | |
| Androecium: | absent |
| Gynoecium: | Present on ray florets |
| Style color: | Yellow-green 154C |
| Style length: | 4 mm |
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Medium |
| Height: | 30 cm |
| Width: | 40-45 cm |
| Stem color: | Greyed-brown 199A |
| Stem strength: | strong |
| Stem brittleness: | not brittle |
| Stem anthocyanin coloration: | absent |
| Internode length: | 1 cm |
| Length of lateral branch: | From top to bottom 20-22 cm |
| Lateral branch color: | Green 137D |
| Lateral branch, attachment: | Weak |
| Lateral branch diameter: | 2 mm |
| Branching (average number of lateral branches): | Prolific with 8 breaks after pinching |
| Natural season blooming date: | September 22 (week 39) |
| **Foliage** | |
| Leaf color: | Upper side: Green 136B<br>Lower side: Green 138B |
| Color midvein: | Upper side: Yellow-green 147D<br>Lower side: Yellow-green 148D |
| Size: | Small; length 3-5.5 cm, width 1.5-2.6 cm |
| Quantity (number per lateral branches): | 20 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Truncate to asymmetric |
| Apex: | Pointed |
| Petiole length: | 0.5-1.2 cm |
| Petiole diameter: | 2 mm |
| Petiole color: | Yellow-green 147D |

TABLE 2

Differences with the comparison variety, when grown under identical conditions

| | 'Zanmucup' | 'Zanmustone' |
|---|---|---|
| Ray floret upperside color | Yellow 12A | Yellow 8A |
| Leaf upperside color | Green 136B | Green 139A-B |

I claim:

1. A new and distinct *chrysanthemum* plant named 'Zanmucup' as described and illustrated.

* * * * *